United States Patent [19]

Auerbach et al.

[11] Patent Number: 5,248,817
[45] Date of Patent: Sep. 28, 1993

[54] PROCESS FOR AROMATIC BROMINATION

[75] Inventors: Joseph Auerbach, Brooklyn, N.Y.; Steven A. Weissman, Little Falls, N.J.

[73] Assignee: Merck & Co., Inc., Rahway, N.J.

[21] Appl. No.: 910,200

[22] Filed: Jul. 8, 1992

Related U.S. Application Data

[63] Continuation-in-part of Ser. No. 730,364, Jul. 15, 1991, abandoned.

[51] Int. Cl.$^5$ .............................................. C07C 65/00
[52] U.S. Cl. .................................... 562/474; 122/493; 122/480; 560/45; 560/47; 560/65; 560/83
[58] Field of Search ...................... 562/474, 493, 480; 560/83, 65, 45, 47

[56]         References Cited
        U.S. PATENT DOCUMENTS 4,232,037  11/1980  Florvall ............................. 424/274
4,789,683  12/1988  Florvall et al. ..................... 514/428

OTHER PUBLICATIONS

CA 77(5):34088g 1972.
CA 100 (17):138334b 1984.
CA 114 (1):6013a 1989.
J. S. Pizey, N-Bromosuccinimide, Synthetic Reagents, 2, 1 (John Wiley New York, 1974).
L. Florvall and Sven-Ove Ogren, J. Med. Chem., 25, 1280 (1982).
V. Oakes et al., J. Chem. Soc., 4678 (1962).

*Primary Examiner*—Paul J. Killos
*Attorney, Agent, or Firm*—Joseph F. DiPrima; Mark R. Daniel; David A. Muthard

[57]            ABSTRACT

A novel procedure for bromination of aromatic moieties utilizes N-bromosuccinimide or dibromodimethylhydantoin in an aqueous alkali medium. The bromination procedure is employed for the preparation of an intermediate used in the preparation of remoxipride, an antipsychotic compound.

23 Claims, No Drawings

PROCESS FOR AROMATIC BROMINATION

RELATED APPLICATION

The present patent application is a continuation-in-part of copending application Ser. No. 730,364, filed Jul. 15, 1991, abandoned.

BACKGROUND OF THE INVENTION

N-Bromosuccinimide (NBS) is a well known synthetic organic reagent which is useful in bromination and/or oxidation of a wide variety organic moieties under a wide variety of reaction conditions. A review of NBS chemistry is found in J.S. Pizey, *Synthetic Reazents*, vol. 2 (John Wiley, New York, 1974) at pages 1-63. While NBS brominations of aromatic moieties have been performed in polar and non-polar organic solvents and in aqueous acidic solution, there have been no reports of NBS brominations utilizing aqueous alkali solutions as the reaction medium. Utilization of such a basic medium has the advantage in that hydrogen bromide, generated in the reaction, is scavenged by the solvent, thereby reducing the possible side reactions associated with its presence in solution. Multiple brominations are also not observed.

Dibromodimethylhydantoin (DBDMH), while not as widely employed as NBS, is a versatile organic reagent (for a review see: Reed, R. A., *Chem. Prod.*, 23, 299 (1960)). It offers the advantage of being more stable and less costly on a bromine equivalent basis than NBS. Previous disclosed brominations of aromatic substrated using DBDMH were run in refluxing CCl$_4$ or CHCl$_3$. DBDMH is also used as a pool disinfectant.

Remoxipride I ((S)-3-bromo-N-[(1-ethyl-2-pyrrolidinyl)methyl]-2,6-dimethoxybenzamide), shown below, is a known antipsychotic agent (U.S. Pat. No. 4,232,037). Preparation of remoxipride typically involves a convergent synthesis wherein a suitably activated 3-bromo-2,6-dimethoxybenzoic acid II is coupled with the enantiomerically pure aminomethyl pyrrolidine III.

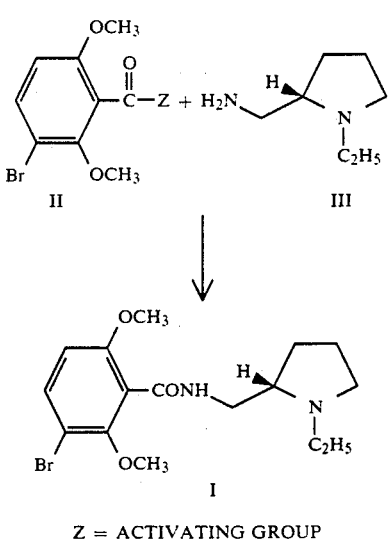

Z = ACTIVATING GROUP

Preparation of Intermediate IVa the precursor of compound II typically involves bromination of commercially available 2,6-dimethoxybenzoic acid employing bromine and dioxane as shown below:

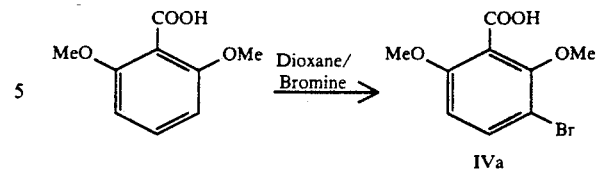

Although good yields of the Intermediate IVa are obtained from the reaction, several impurities, shown below, result from the further reaction of the product and bromine and/or the hydrogen bromide generated in the reaction.

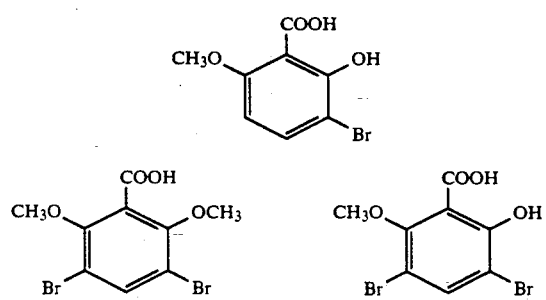

SUMMARY OF THE INVENTION

The instant invention provides an improved bromination process for the preparation of brominated aromatic compounds which results in quantitatively fewer of the impurities that are associated with previous disclosed bromination processes.

The instant invention also provides a novel reaction condition for bromination of aromatic compounds with N-bromosuccinimide or dibromodimethylhydantoin wherein the solvent is an aqueous alkali solution.

Further, the instant invention to provides an improved process for the preparation of 3-bromo-2,6-dimethoxybenzoic acid having higher yields and fewer impurities than processes previously known in the art.

DETAILED DESCRIPTION OF THE INVENTION

The present invention provides a novel process for the preparation of a bromoaromatic compound, having the formula IV:

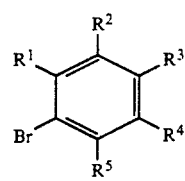

wherein:
$R^1$, $R^2$, $R^4$, and $R^5$ are independently selected from:
(a) hydrogen,
(b) $C_1$-$C_6$-alkyl,
(c) $C_1$-$C_6$-alkoxy,
(d) —OH,
(e) —CO$_2$H,
(f) —CO$_2$(C$_1$-C$_6$-alkyl),
(g) —N(C$_1$-C$_6$-alkyl)$_2$,
or $R^1$, $R^2$, $R^3$, $R^4$, or $R^5$ on adjacent ring carbons may be combined to form a —O—(CH$_2$)$_n$—O— residue;

provided that at least one of $R^1$, $R^2$, $R^4$, or $R^5$ is —$CO_2H$;

$R^3$ is $C_1$-$C_6$-alkoxy or —$N(C_1$-$C_6$-alkyl$)_2$, or $R^2$ and $R^3$ or $R^3$ and $R^4$ are combined to form a —O—$(CH_2)_n$—O— residue; and n is 1 to 3;

which comprises:

treating an aromatic compound of the formula V:

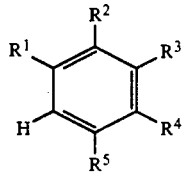

wherein the substituents $R^1$, $R^2$, $R^3$, $R^4$, and $R^5$ are as described herein above;

in an aqueous alkali solution with a brominating agent selected from:

(a) N-bromosuccinimide, and (b) 1,3-dibromo-5,5-dimethylhydantoin;

at a temperature and for a length of time sufficient to optimally convert the compound of formula V to the compound of formula IV or a salt thereof; and then optionally treating the reaction mixture with an acid to form the compound of formula IV.

The term "aqueous alkali solution" includes solution of an alkali base in an aqueous solvent and the like.

The term "alkali base" includes strong alkali bases, which include sodium hydroxide, lithium hydroxide, potassium hydroxide and the like. A preferred alkali base is sodium hydroxide.

The term "aqueous solvent" includes water and solutions of water and a water miscible co-solvent(s). The term "water miscible co-solvent" includes low-molecular-weight alcohols, dimethoxyethane, tetrahydrofuran and the like. A preferred aqueous solvent is water.

The term "low-molecular-weight alcohol" includes hydroxyalkane compounds having from 1 to 4 carbon atoms and includes branched and straight chain alcohols. The term includes methanol, ethanol, iso-propanol and the like.

The term "temperature . . . sufficient to optimally convert the compound of the formula V to a salt of the compound of formula IV" represents a temperature sufficiently high to maintain conversion of the starting material V but also sufficiently low to avoid decomposition of the starting material and the product. The term includes temperatures between 0° and 30° C. A preferred temperature is between 23° and 29° C.

The term "length of time sufficient to optimally convert the compounds of the formula V to a salt of the compound of the formula IV" represents a period of time sufficiently long to convert the maximum amount of the starting material to the salt of the compound of the formula IV. The term includes times of 1 to 40 hours. A preferred length of time is a time length between 4 and 25 hours.

The term "a salt of the compound of formula IV" includes the salt of a carboxylic acid moiety of the product IV (if such a moiety is present) which corresponds to the alkali base employed in the aqueous alkali solution. The term includes the sodium salt, lithium salt, potassium salt and the like.

The term "acid" includes anhydrous acids and aqueous acidic solutions.

The term "anhydrous acid" includes gaseous mineral acids such as hydrogen bromide, hydrogen chloride and the like.

The term "aqueous acidic solution" includes solutions of a mineral acid or sulfuric acid in an aqueous solvent. The term "mineral acid" includes hydrogen chloride, hydrogen bromide and the like. A preferred aqueous acidic solution is aqueous hydrobromic acid.

One embodiment of the process of the instant invention is that process wherein the brominating agent employed is N-bromosuccinimide in an amount selected from a value in the range between 1.0 to 1.5 molar equivalents with respect to starting aromatic compound V.

In a class of this embodiment is the process wherein the amount of the alkali base in the aqueous alkali solution employed is selected from a value in the range between 1.0 and 3.5 molar equivalents with respect to starting aromatic compound V.

In a subclass of this class of the instant invention is the process wherein the ratio of the molar equivalent amount of alkali base remaining after any acid moiety present in the starting aromatic compound V has been neutralized to the molar equivalent of N-bromosuccinimide utilized is selected from a value in the range between 1.0 and 1.25.

In another class of this embodiment is the process of the instant invention wherein the acid treated reaction mixture is cooled and filtered to provide the compound of the formula IV.

In another class of this embodiment is the process of the instant invention wherein the acid treated reaction mixture is extracted with a suitable organic solvent which after washing, drying and evaporating to dryness provides the compound of the formula IV.

Another embodiment of the instant invention is that process wherein the brominating agent employed is dibromodimethylhydantoin in an amount selected from a value in the range between 0.505 to 0.55 molar equivalents with respect to starting aromatic compound V.

In a class of this embodiment is the process wherein the amount of the alkali base in the aqueous alkali solution employed is selected from a value in the range between 1.01 and 1.1 molar equivalents with respect to starting aromatic compound V.

In a subclass of this class of the instant invention is the process wherein the ratio of the molar equivalent amount of alkali base remaining after any acid moiety present in the starting aromatic compound V has been neutralized to the molar equivalent of N-bromosuccinimide utilized is selected from a value in the range between 0.1 and 1.25.

One embodiment of the instant invention is the process for the preparation of a bromobenzoic acid, having the formula IVa:

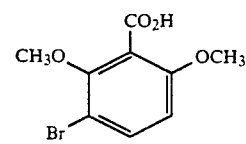

which comprises:

treating a benzoic acid of the formula Va:

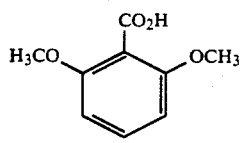

in an aqueous alkali solution
WITH N-bromosuccinimide at a temperature and for a length of time sufficient to optimally convert the compound of formula Va to the compound of formula IVa or a salt of the compound of formula IVa; and
then optionally treating the reaction mixture with an acid.

One class of this embodiment of the process of the instant invention is that process wherein the amount of N-bromosuccinimide employed is selected from a value in the range between 1.0 to 1.5 molar equivalents with respect to starting 2,6-dimethoxybenzoic acid.

In a subclass of this embodiment is the process wherein the amount of the alkali base in the aqueous alkali solution employed is selected from a value in the range between 2.0 and 2.5 molar equivalents with respect to starting 2,6-dimethoxybenzoic acid.

Exemplifying this subclass of this class of the instant invention is the process wherein the ratio of the molar equivalent amount of alkali base remaining after the acid moiety of the 2,6-dimethoxybenzoic acid has been neutralized to the molar equivalent of N-bromosuccinimide utilized is selected from a value in the range between 1.0 and 1.25.

In another subclass of this embodiment is the process of the instant invention wherein the acid treated reaction mixture is cooled and filtered to provide the compound of the formula IVa.

In another subclass of this embodiment is the process of the instant invention wherein the acid treated reaction mixture is extracted with a suitable organic solvent which after washing, drying and evaporating to dryness provides the compound of the formula IVa.

The following synthetic Scheme 1 illustrates a reaction sequence in which the process of the instant invention is employed. It is understood that this scheme is meant to be illustrative and is not limiting.

SCHEME 1

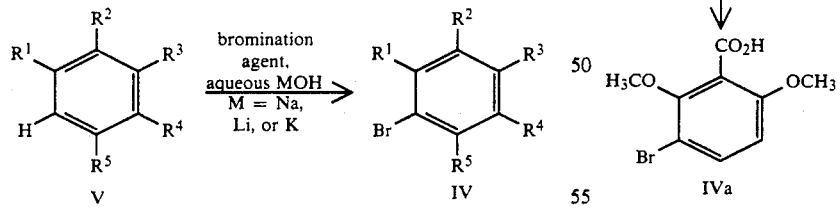

In words relative to the equations, the aromatic compound of the formula V is dissolved in an aqueous alkali solution containing a excess amount of equivalents of base, such as aqueous NaOH solution, aqueous KOH solution, methanolic aqueous NaOH and the like. The solution is then treated with a suitable brominating agent, such as N-bromosuccinimide or 1,3-dibromo-5,5-dimethyl- hydantoin, and the reaction mixture is stirred at room temperature for a period of time, such as 2 hours to 24 hours. The reaction mixture is then tested by a potassium iodide starch paper test (SPT) [starch iodide test paper that has been wetted with aqueous acetic acid; 1/1; v/v] and if the test is positive, an oxidant-neutralizing salt, such as sodium sulfite and the like, is added. The reaction mixture is then treated with an acid or an acidic aqueous solution and cooled in an ice bath. If the product formed is insoluble in the work-up solution, filtration of the mixture provides the crude product IV which may be used as is in a subsequent reaction or further purified. If isolation by filtration is not appropriate a standard organic solvent extractive work-up may be employed.

The following synthetic Scheme 2 illustrates a reaction sequence in which the process of an embodiment of the instant invention is employed. It is understood that this scheme is meant to be illustrative and is not limiting.

SCHEME 2

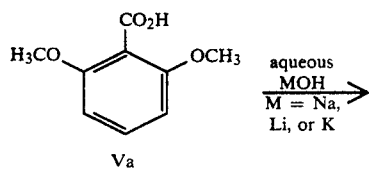

Va

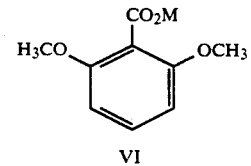

VI

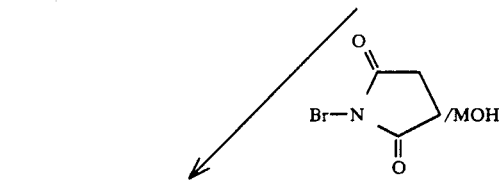

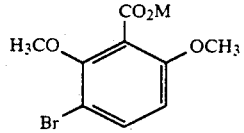

H+

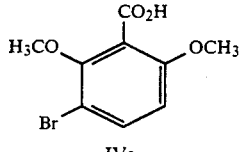

IVa

In words relative to the equations, 2,6-dimethoxybenzoic acid Va is dissolved in an aqueous alkali solution containing a excess amount of equivalents of base, such as aqueous NaOH solution, aqueous KOH solution and the like, to provide a alkaline solution of the salt VIE. The solution is then treated with N-bromosuccinimide (NBS) and the reaction mixture is stirred at room temperature for a period of time, such as 2 hours to 24 hours. The reaction mixture is then tested by a potassium iodide starch paper test (SPT) [starch iodide test paper that has been wetted with aqueous acetic acid; 1/1; v/v] and if the test is positive, an oxidant-neutralizing salt, such as sodium sulfite and the like, is added. The reaction mixture is then treated with an acid or an acidic aqueous solution and cooled in an ice bath. Filtration of the mixture provides the crude product IVa which may be used as is in a subsequent reaction or further purified.

The following synthetic Scheme 3 illustrates a reaction sequence in which the process of the instant invention is employed in the synthesis of remoxipride. It is understood that this scheme is meant to be illustrative and is not limiting

SCHEME 3

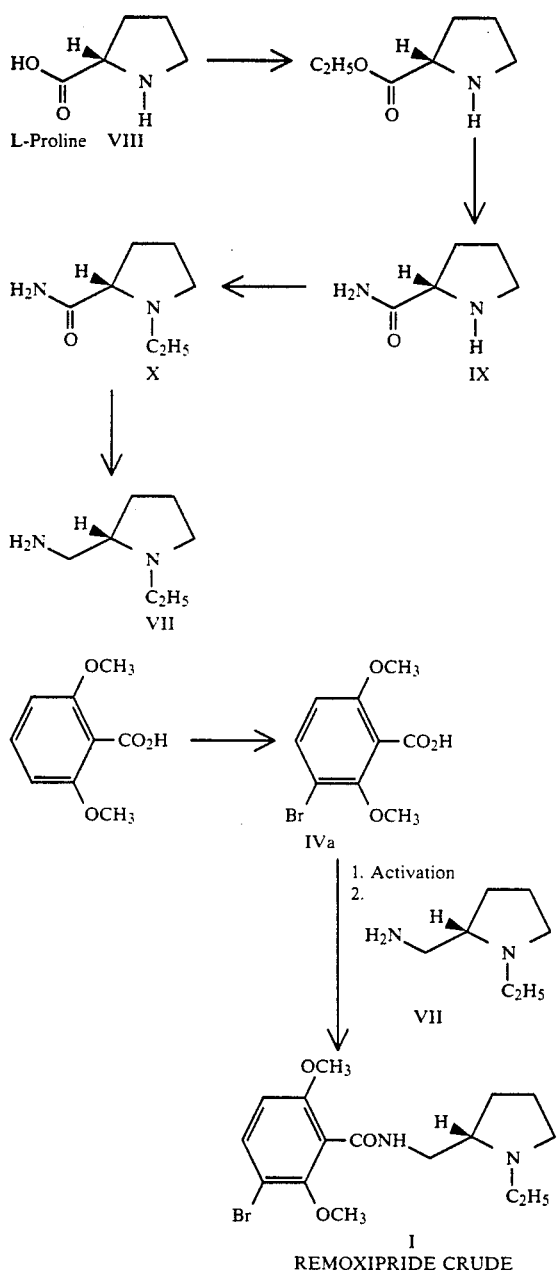

In words relative to the equations, the aminomethylpyrrolidine component VII of remoxipride is prepared from enantiomerically pure L-proline VIII. To this end L-proline is esterified and the ester treated with ammonia in a suitable solvent, such as methanol, ethanol and the like, to provide the amide IX. The amide is ring N-ethylated by treating it with an aklylating agent such as ethyl bromide and the like, in the presence of a base, such as potassium carbonate, sodium carbonate, and the like, in a suitable solvent such as ethanol. The amide X is subsequently reduced with a suitable reducing agent, such as lithium aluminum hydride and the like, to provide compound VII.

The bromodimethoxybenzoic acid IVa, prepared as described in Scheme 2, is treated with an activating reagent, such as thionyl chloride, carbonyl diimidazole and the like, to provide an activated acid which is reacted, without isolation, with compound VII, to provide crude remoxipride I.

The invention is further defined by reference to the following Examples 1 through 4, which are meant to be illustrative and not limiting. Example 1, Method F, is provided as representative of previously known preparations of the intermediate IVa, and is included for comparison with the process of the embodiment of the instant invention. All temperatures are in degrees Celsius. All purity percentages of the crude product are weight percentages and were determined by HPLC (YMC AQ-301 column (S-5 120A ODS) reverse phase; mobile phase: 58% 0.07M pH 1.8 phosphate buffer, 48% CH$_3$CN; 225 nm detection) and yields of the desired product are given based on pure mono-brominated product. All impurity percentages disclosed were determined by HPLC and are area percentages relative to the desired product.

EXAMPLE 1

Preparation of 3- Bromo-2,6-dimethoxybenzoic Acid

Method A: Preparation Using N-Bromosuccinimide and Aqueous Sodium Hydroxide at 2 hours 10 min. Duration A 500 mL round-bottomed 4-necked 24/40 ST: reaction vessel, fitted with a mechanical stirrer and digital thermometer, was charged with 8.0 grams of powdered 2,6-dimethoxybenzoic acid (DMBA) (Aldrich-99%, 43.473 mmol), 50 mL of deionized water and 18.25 mL (2.1 equiv.) of aqueous 5N NaOH soln. The mixture was stirred, dissolving the acid and the temperature rose to 30° C. The solution was cooled to 2° C. with an ice water bath and maintained at that temperature. Then 8.20 grams of powdered N-bromosuccinimide (Aldrich 99%), was added with brisk stirring to the cold solution. The reaction temperature rose to 8° C. over two minutes then cooled back to 4° C. over an additional 4 minutes. The cooling bath was removed and the reaction was allowed to warm to room temperature reaching 21° C. after 0.5 hr. and 26° C. after about one hour. The temperature rose to 27° to 28° C. for the remaining reaction time. The total time since NBS addition was 2 hr. 10 min.

The reaction at this point gave a positive potassium iodide starch paper test (SPT). The reaction was then treated with 0.5 gm Na$_2$SO$_3$ which resulted in a negative SPT. The reaction was diluted with 50 mL of water and was treated, in portions, with 12 mL concentrated aqueous HBr (2.43 equiv.) causing precipitation of the product. The mixture was cooled to ice bath temperature and filtered off (fritted glass funnel, M porosity). The solid was slurried and washed in portions with 125 mL of ice cold pure water (the pH at the end of the filtration rose to 3° C. The precipitate was suction dried under a nitrogen stream and then dried overnight under high vacuum at 75° C. The product weighed 9.95 gm. which by HPLC analysis contained 1.1 wt. % of unreacted starting material/1.4% yield and 97.9 wt. % of the desired monobrominated product/85.8% yield and no detectable water by Karl Fischer (KF) titration.

Method B: Preparation Using N-Bromosuccinimide and Aqueous Sodium Hydroxide at 4 hour 20 min. Duration A 5 liter round bottomed 4 neck 24/40 ST. reaction vessel, fitted with a mechanical stirrer and digital thermometer, was charged with 104 grams of powdered 2,6-dimethoxybenzoic acid (Aldrich 99%), (565 mmol) 255 mL of 5N aqueous NaOH, (1275 mmol, 2.256 equiv.) and 650 mL of water. The mixture was stirred to dissolve the DMBA then cooled to 0° C. with an ice/MeOH bath. To the reaction mixture was added powdered N-bromosuccinimide (Aldrich 99%) (121.9 grams, 1.2 equiv.) in portions: ninety grams of NBS was added over two minutes and the reaction temperature rose to 5° C. then another 31.9 grams was added. The reaction mixture was cooled to 2° C. then the cooling bath was removed allowing the reaction temperature to rise to room temperature. After 4 hr. and 20 min. the reaction gave a positive SPT. The reaction mixture was treated with 8 grams of sodium sulfite which resulted in a negative SPT. The insolubles were filtered from the reaction mixture and the filtrate returned to the reaction vessel. An additional 650 mL of water was added to the filtrate. Concentrated 48% aqueous hydrobromic acid (167.57 mL, 2.6 equiv.) was added to the reaction mixture over 1 min. which caused the product to precipitate. The thick reaction mixture was diluted with 500 mL of water and cooled to 0°–5° C., then filtered through a 3 liter filter funnel with a (M) porosity fritted disk. The solid was washed with an additional 1150 mL of water in portions. The last filtrates gave a weak positive test for bromides. The solid was suction dried under nitrogen then under high vacuum at 60° C. overnight to provide 140.8 grams of the desired product (92.7% yield; 97.1% wt. % pure containing 0.29 wt. % of unreacted starting material and no detectable water by KF titration).

Method C: Preparation Using N-Bromosuccinimide and Aqueous Sodium Hydroxide at 21 hour 34 min. Duration A 5 liter round-bottomed 4-necked 24/40 ST. reaction vessel, fitted with a mechanical stirrer and digital thermometer, was charged with 104 grams of powdered 2,6-dimethoxybenzoic acid (Aldrich 99%, 565.1 mmol), 255 mL of 5N aqueous NaOH (1275 mmol, 2.256 equiv.) and 650 mL of water. The mixture was stirred to dissolve the DMBA then cooled to 1° C. To the reaction mixture was added powdered N-bromosuccinimide (121.93 grams, Aldrich 99%, 1.2 equiv) in portions: about 90 grams was added over three minutes and the reaction temperature rose to 8° C. The reaction temperature then decreased to 6° C. and the remaining NBS was added. The temperature rose again to 8° C. and then the reaction mixture cooled down to 3° C. and the ice/water cooling bath was removed. The temperature of the reaction mixture was allowed to rise to room temperature. After 21 hr. 34 min. the reaction mixture gave a weakly positive SPT. The reaction mixture is treated with 2.0 grams of sodium sulfite which resulted in a negative SPT. The reaction mixture was filtered to remove a small amount of insoluble matter. The filtered reaction mixture was returned to a clean 5 liter reaction vessel and diluted with 650 mL of water. To the stirred reaction mixture was added 167.57 mL of concentrated 48% aqueous HBr over three minutes. A copious precipitate formed. The mixture was stirred and cooled to 3° C. and the solids were filtered off through a 3 L (M) porosity funnel with a fritted disk. The solid was washed with 1352 mL of ice cold water in portions then dried with suction under nitrogen and then overnight at 60° C. under high vacuum. The isolated product weight was 142.9 grams 94.82% yield/97.91 wt. % pure which when corrected for sample used in HPLC reaction monitoring calculates to 143.7 grams/95.4% yield. The product contained residual starting material of 0.14 HPLC area % and no detectable water by KF titration. The following impurities were detected by HPLC in the crude product: succinimide: 0.573 area %; 3,5-dibromo-2,6-dimethoxybenzoic acid: 0.146 area %; and 3,5-dibromo-2-hydroxy-6-methoxybenzoic acid: 0.012 area %.

Method D: Preparation Using N-Bromosuccinimide and Aqueous Potassium Hydroxide

A 500 mL round-bottomed 4-necked 24/40 ST. reaction vessel, fitted with a mechanical stirrer and digital thermometer, was charged with 8.0 grams of powdered 2,6-dimethoxybenzoic acid (Aldrich 99%, 43.473 mmol), 7.02 gm. potassium hydroxide (86.8% pure, 2.5 equiv., 108.68 mmol) and 45 mL of water. The reaction mixture was stirred and heated to 50° C. to solubulize the mixture. The mixture was cooled to 1° C. and 9.38 grams of powdered N-bromosuccinimide, (99% pure, 1.2 equiv.) was added to the reaction mixture. The temperature of the reaction mixture rose to 10° C. and then the cooling bath was removed. The reaction was warmed to room temperature and was stirred for a total of 27 hours. The reaction at this point gave a weakly positive SPT. The reaction mixture was treated with 1 gm of sodium sulfite which resulted in the reaction mixture giving a negative SPT. The reaction mixture was cooled to 0°–1° C. and was acidified with 15.95 mL of concentrated hydrobromic acid (added in portions over 1 min.). The copious precipitated reaction mixture was filtered cold through a fritted glass suction funnel. The filtrate was used to aid in the transfer, then the precipitate was washed with 125 mL of ice cold 1N aqueous HBr in portions, then suction dried under nitrogen. The precipitate was dried overnight at 60° C. The product weighed 10.5 gm which by HPLC analysis contained 1.9 wt. % of unreacted starting material/2.6% yield and 90.1 wt. % of the desired product (83.3% yd.) and no detectable water by KF titration.

Method E: Preparation Using Dibromodimethylhydantoin and Sodium hydroxide 2,6-Dimethoxybenzoic acid (99.0 g, 538 mmols) is stirred with 500 mL of water at room temperature, followed by the addition of 5N aqueous NaOH (110 mL, 550 mmol). The resulting orange solution is cooled to 20° C. by a cold water bath and DBDMH (80.2 g, 272.1 mmols) is added in portions over 5 min. while maintaining the internal temperature at <25° C. The mixture was allowed to stir at 20°–25° C. for 4.5 hours and worked up as described in Method A hereinabove. The crude product was recrystallized from aqueous ethanol to provide 122.6 g of the desired product. Analytical evaluation of the product and the mother liquors from the recrystallization indicated a 90.0% assay yield of the 3-bromo-2,6-dimethoxybenzoic acid and a 2.1% assay yield of 3,5-dibromo-2,6-dimethoxybenzoic acid.

Method F: Preparation Using Bromine in Dioxane (Illustrative of Prior Process)

A 2 liter round-bottomed flask was charged with 72 grams of 2,6-dimethoxybenzoic acid (99%, 391.2 mmol) and 237 grams of dioxane. The solution was cooled to 15° and bromine (62.11 grams, 99.5%, 1 equiv.) was added dropwise over 2 hours while the temperature was maintained at 17° to 19° C. The reaction mixture was stirred at 20° C. for 2 hours, then 90 mL of water was added dropwise over 30 mins. to the mixture. The mixture was then cooled to 15° C. and an additional 834 mL of water was added dropwise over a 2 hour period. The reaction mixture was aged at 15° C. for 3 hours and the solid which formed was collected by filtration and washed with 60 mL of water. The solid was dried under high vacuum at 70° C. for 12 hours to provide 87.9 g of the crude desired product (93.0% pure, 79% yield). The following impurities were detected by HPLC in the crude reaction product: 3,5-dibromo-2,6-dimethoxybenzoic acid: 0.385 area %; 3,5-dibromo-2-hydroxy-6-methoxybenzoic acid: 4.05 area %; and 3-bromo-2-hydroxy-6-methoxy benzoic acid: 2.91 area %.

EXAMPLE 2

Synthesis of 2-Bromo-3,4,5-trimethoxybenzoic Acid

Using the procedure described herein above in Example 1, Method E, 3,4,5-trimethoxybenzoic acid was brominated with DBDMH to provide the following results (assay yields) after reacting for 25 hours at 20°-25° C.:
2-bromo-3,4,5-trimethoxybenzoic acid: 91.1%;
3,4,5-trimethoxybenzoic acid: 3.7%;
2,6-dibromo-3,4,5-trimethoxybenzoic acid: 2.0%.

EXAMPLE 3

Synthesis of 6-Bromo-2,3-dimethoxybenzoic Acid

Using the procedure described herein above in Example 1, Method E, 2,3-dimethoxybenzoic acid was brominated with DBDMH to provide the following results (assay yields) after reacting for 22 hours at 20°-25° C:
6-bromo-2,3-dimethoxybenzoic acid: 90.3%;
2,3-dimethoxybenzoic acid: 7.7%;
5-bromo-2,3-dimethoxybenzoic acid: 2.5%.

EXAMPLE 4

Synthesis of 2-Bromopiperonylic Acid

Using the procedure described herein above in Example 1, Method E, piperonylic acid was brominated with DBDMH to provide the following results (assay yields) after reacting for 22 hours at 20°-25° C.:
2-bromopiperonylic acid: 86.0%;
piperonylic acid: 7.7%.

EXAMPLE 5

Synthesis of 5-Bromo-2-methoxybenzoic Acid
Method A: Bromination with N-Bromosuccinimide and NaOH o-Anisic acid (4.56 g, 30 mmols) was charged in a 250 mL flask and a solution of 2.64 g (66 mmol) of NaOH in 47 mL of water was added. The anisic acid was dissolved with stirring and the solution then cooled to 0° to 5° C. with an ice/methanol bath. NBS (6.41 g, 36 mmol) was added in portions to the reaction flask and after the addition was complete the reaction was allowed to warm to room temperature. The reaction was stirred at room temperature for 48 hours and was monitored by analytical LC during this time. At the end of the 48 hours another 0.2 equiv. (5 mmol) of NBS was added to the reaction mixture and the reaction mixture was stirred at room temperature for an additional 7 hours.

Workup as described in Example 1, Method A, provided 7.34 g of a solid (98.5% pure by HPLC, 1.5% of solid is unreacted starting material; 93% yield.) The filtrate from the solid contains another 2% yield of brominated product.

Method B: Bromination with Dibromodimethylhydantoin and NaOH.

Using the procedure described herein above in Example 1, Method E, o-anisic acid was brominated with DBDMH to provide the following results (assay yields) after reacting for 18 hours at 20°-25° C.:
5-bromo-2-methoxybenzoic acid: 98%.

the isolated product contains 0.3 wt % of unreacted product.

What is claimed is:

1. A process for the preparation of a compound having the formula IV:

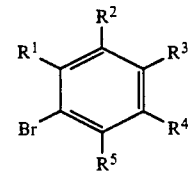

or an alkali salt thereof;
wherein:
$R^1$, $R^2$, $R^4$, and $R^5$ are independently selected from:
(a) hydrogen,
(b) $C_1$-$C_6$-alkyl,
(c) $C_1$-$C_6$-alkoxy,
(d) —OH,
(e) —$CO_2H$,
(f) —$CO_2(C_1$-$C_6$-alkyl),
(g) —$N(C_1$-$C_6$-alkyl)$_2$,
or $R^1$, $R^2$, $R^3$, $R^4$, or $R^5$ on adjacent ring carbons may be combined to form a —O—$(CH_2)_n$—O— residue;
provided that at least one of $R^1$, $R^2$, $R^4$, or $R^5$ is —$CO_2H$;
$R^3$ is $C_1$-$C_6$-alkoxy or —$N(C_1$-$C_6$-alkyl)$_2$, or $R^2$ and $R^3$ or $R^3$ and $R^4$ are combined to form a —O—$(CH_2)_n$—O— residue; and
n is 1 to 3;
which comprises:
treating an aromatic compound of the formula V:

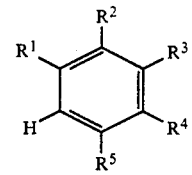

in an aqueous alkali solution
with a brominating agent selected from:
(a) N-bromosuccinimide, and
(b) 1,3-dibromo-5,5-dimethylhydantoin;
at a temperature and for a length of time sufficient to optimally convert the compound of formula V to the compound of formula IV or a salt thereof; and
then optionally treating the reaction mixture with an acid to afford the compound of formula IV.

2. The process of claim 1 wherein the amount of the brominating agent employed is selected from a value in the range between 0.505 to 1.5 molar equivalents with respect to the compound of the formula V.

3. The process of claim 1 wherein the brominating agent is N-bromosuccinimide.

4. The process of claim 3 wherein the aqueous alkali solution is a solution of sodium hydroxide in water.

5. The process of claim 3 wherein the aqueous alkali solution is a solution of potassium hydroxide in water.

6. The process of claim 1 wherein the acid is an aqueous acidic solution.

7. The process of claim 6 wherein the aqueous acidic solution is aqueous hydrobromic acid.

8. The process of claim 6 wherein the aqueous acidic solution is aqueous hydrochloric acid.

9. The process of claim 1 wherein the brominating agent is 1,3-dibromo-5,5-dimethylhydantoin.

10. The process of claim 9 wherein the amount of the 1,3-dibromo-5,5-dimethylhydantoin utilized in the process relative to the amount of compound V is selected from 0.505 to 0.55 molar equivalents amd the amount of alkali base in the aqueous alkali solution relative to the amount of compound V is selected from 1.01 to 1.1 molar equivalents.

11. The process of claim 9 wherein the aqueous alkali solution is a solution of sodium hydroxide in water.

12. A process for the preparation of a compound, having the formula IVa:

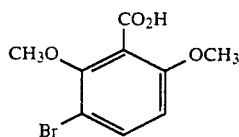
IVa which comprises:
treating a benzoic acid of the formula Va:

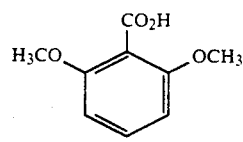
Va in an aqueous alkali solution with a brominating agent selected from:
(a) N-bromosuccinimide, and
(b) 1,3-dibromo-5,5-dimethylhydantoin;
at a temperature and for a length of time sufficient to optimally convert the compound of formula Va to the compound of formula IVa or a salt of the compound of formula IVa; and
then optionally treating the reaction mixture with an acid.

13. The process of claim 12 wherein the amount of the brominating agent employed is selected from a value in the range between 0.505 to 1.5 molar equivalents with respect to the compound of the formula Va.

14. The process of claim 12 wherein the brominating agent is N-bromosuccinimide.

15. The process of claim 14 wherein the aqueous alkali solution is selected from: a solution of sodium hydroxide in water or a solution of potassium hydroxide in water.

16. The process of claim 12 wherein the temperature is selected from a temperature between 23° and 29° C.

17. The process of claim 12 wherein the acid is an aqueous acidic solution.

18. The process of claim 17 wherein the aqueous acidic solution is aqueous hydrobromic acid.

19. The process of claim 17 wherein the aqueous acidic solution is aqueous hydrochloric acid.

20. The process of claim 12 wherein the compound having the formula IVa is subsequently employed in the preparation of remoxipride.

21. The process of claim 12 wherein the brominating agent is 1,3-dibromo-5,5-dimethylhydantoin.

22. The process of claim 21 wherein the amount of the 1,3-dibromo-5,5-dimethylhydantoin utilized in the process relative to the amount of compound Va is selected from 0.505 to 0.55 molar equivalents amd the amount of alkali base in the aqueous alkali solution relative to the amount of compound Va is selected from 1.01 to 1.1 molar equivalents.

23. The process of claim 21 wherein the aqueous alkali solution is a solution of sodium hydroxide in water.

* * * * *